United States Patent
Harada et al.

(10) Patent No.: US 11,617,540 B2
(45) Date of Patent: Apr. 4, 2023

(54) SENSOR CONNECTOR APPARATUS FOR USE IN ELECTROENCEPHALOGRAPHIC SPECTRUM ANALYZER, PROVIDED WITH CONDUCTIVE CONNECTION ELECTRODES CONNECTED TO SENSOR ELECTRODES

(71) Applicant: KURUME UNIVERSITY, Fukuoka (JP)

(72) Inventors: Hideki Harada, Kurume (JP); Seiya Muta, Kurume (JP); Misa Ukeda, Kurume (JP); So Ota, Kurume (JP); Maiko Hirata, Kurume (JP)

(73) Assignee: KURUME UNIVERSITY, Fukuoka (JP)

( * ) Notice: Subject to any disclaimer, the term of this patent is extended or adjusted under 35 U.S.C. 154(b) by 1001 days.

(21) Appl. No.: 16/348,265

(22) PCT Filed: Nov. 7, 2017

(86) PCT No.: PCT/JP2017/040131
§ 371 (c)(1),
(2) Date: May 8, 2019

(87) PCT Pub. No.: WO2018/088400
PCT Pub. Date: May 17, 2018

(65) Prior Publication Data
US 2019/0313973 A1 Oct. 17, 2019

Related U.S. Application Data

(60) Provisional application No. 62/420,202, filed on Nov. 10, 2016.

(51) Int. Cl.
*A61B 5/00* (2006.01)
*A61B 5/291* (2021.01)
*A61B 5/374* (2021.01)

(52) U.S. Cl.
CPC ............ *A61B 5/6833* (2013.01); *A61B 5/291* (2021.01); *A61B 5/374* (2021.01); *A61B 2562/222* (2013.01); *A61B 2562/227* (2013.01)

(58) Field of Classification Search
CPC ....... A61B 5/6833; A61B 5/291; A61B 5/374; A61B 2562/227; A61B 5/369; A61B 2562/222
See application file for complete search history.

(56) References Cited

U.S. PATENT DOCUMENTS

2003/0091096 A1  5/2003  Agrawal et al.
2009/0105577 A1*  4/2009  Wu ........................ A61B 5/291
                                                          600/383
(Continued)

FOREIGN PATENT DOCUMENTS

JP  2005-509464  4/2005
JP  2013-121489  6/2013
(Continued)

OTHER PUBLICATIONS

International Search Report dated Jan. 30, 2018 in International (PCT) Application No. PCT/JP2017/040131.
(Continued)

*Primary Examiner* — Eric F Winakur
*Assistant Examiner* — Abid A Mustansir
(74) *Attorney, Agent, or Firm* — Wenderoth, Lind & Ponack, L.L.P.

(57) ABSTRACT

A sensor connector apparatus is disclosed to connected between an electroencephalographic spectrum analyzer and a sensor for use in the electroencephalographic spectrum analyzer. The sensor connector apparatus includes sensor connectors. Each of the sensor connectors includes: a connector to be connected to the electroencephalographic spectrum analyzer; a connector lead where the connector is
(Continued)

connected to one end of the connector lead; and a conductive connector electrode that is connected to another end of the connector lead, and is connected to a sensor electrode of the sensor. The electroencephalographic spectrum analyzer is a bispectral index (BIS) processor, the sensor is a BIS Quatro sensor to be connected to the BIS processor, and the connector is connected to a sensor electrode of the BIS Quatro sensor.

5 Claims, 13 Drawing Sheets

(56) References Cited

U.S. PATENT DOCUMENTS

| | | | |
|---|---|---|---|
| 2012/0253163 | A1 | 10/2012 | Afanasewicz et al. |
| 2013/0079618 | A1* | 3/2013 | Sandmore ............ A61B 5/6839 29/402.08 |

FOREIGN PATENT DOCUMENTS

| | | |
|---|---|---|
| JP | 2016-86972 | 5/2016 |
| WO | 2012/017950 | 2/2012 |

OTHER PUBLICATIONS

English translation of International Preliminary Report on Patentability dated May 23, 2019 in International (PCT) Application No. PCT/JP2017/040131.
Anaesthesia UK: Bispectral index (BIS), [online], Jul. 30, 2016 (archive), retrieval date Jan. 4, 2018, Internet, <URL: http://web.archive.org/web/20160730091906/http://www.frca.co.uk/article/aspx?articleid=100502>.
A. A. Dahaba et al., "BIS-vista occipital montage in patients undergoing neurosurgical procedures during propofol-remifentanil anesthesia", Anesthesiology, vol. 112, No. 3, Mar. 2010, pp. 645-651.
Shin Young Lee et al., "Comparison of bispectral index scores from the standard frontal sensor position with those from an alternative mandibular position", Korean Journal of Anesthesiology (Kja), vol. 66, No. 4, Apr. 2014, pp. 267-273.
B. Brown et al., "Acceptability of auricular vs frontal bispectral index values", British Journal of Anaesthesia (BJA), vol. 113, Issue 2, Aug. 1, 2004, pp. 296.
Nihon Kohden Corporation, "BIS Processor QE-910P", Visceral Function Test Instrument, Controlled Medical Device, Controlled Medical Device Requiring Special Maintenance, and Electroencephalographic Spectrum Analyzer, revised in Apr. 2017 (Eight Edition), [Searched on Sep. 29, 2017], Internet <URL http://www.nihonkohden.co.jp/iryo/documents/pdf/H904285E.pdf> (with partial English translation).
Nihon Kohden Corporation, "BIS Monitor Vista A-3000", Visceral Function Test Instrument, Controlled Medical Device, Controlled Medical Device Requiring Special Maintenance, and Electroencephalographic Spectrum Analyzer, Revised on Nov. 8, 2010 (Second Edition), [Searched on Sep. 29, 2017], Internet <URL http://nihondohken.co.jp./iryo/documents/pdf/HJ00114A.pdf> (with partial English translation).
Covidien Japan Inc., "BIS Quatro Sensor", Visceral Function Test Instrument, Electroencephalographic Recording from Scalp Electrode, and General Medical Device, Revised on Jul. 2, 2012 (Sixth Edition), [Searched on Sep. 29, 2017], Internet <URL http://www.covidien.co.jp/product_service/documents_pdf/RS-A5BISSN02(06).pdf> (with partial English translation).

* cited by examiner

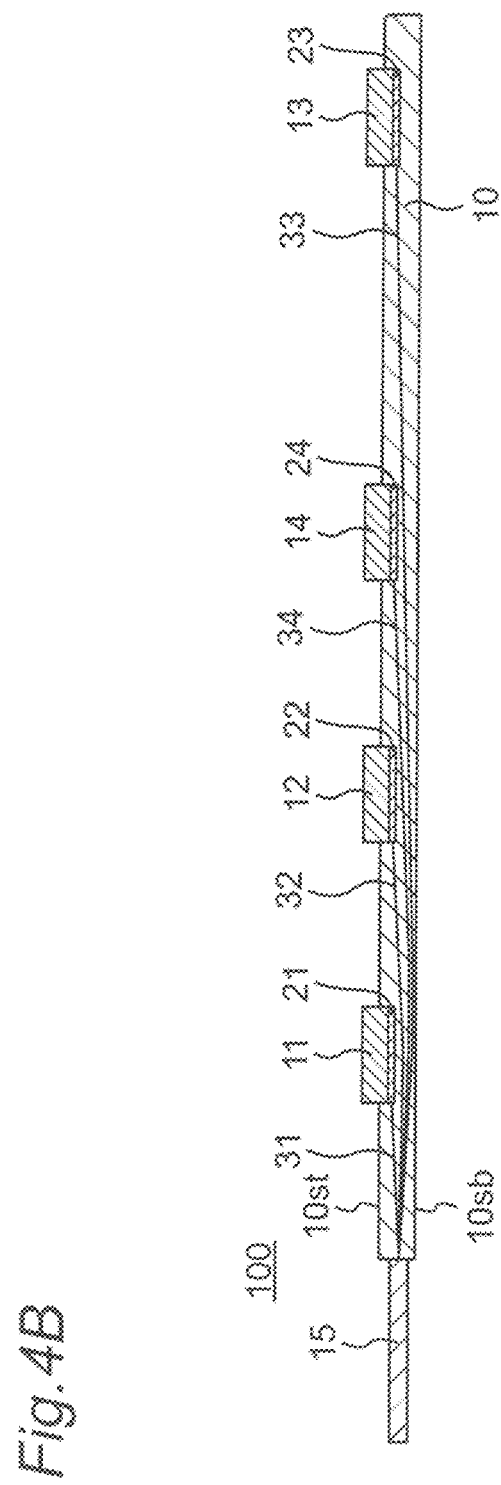

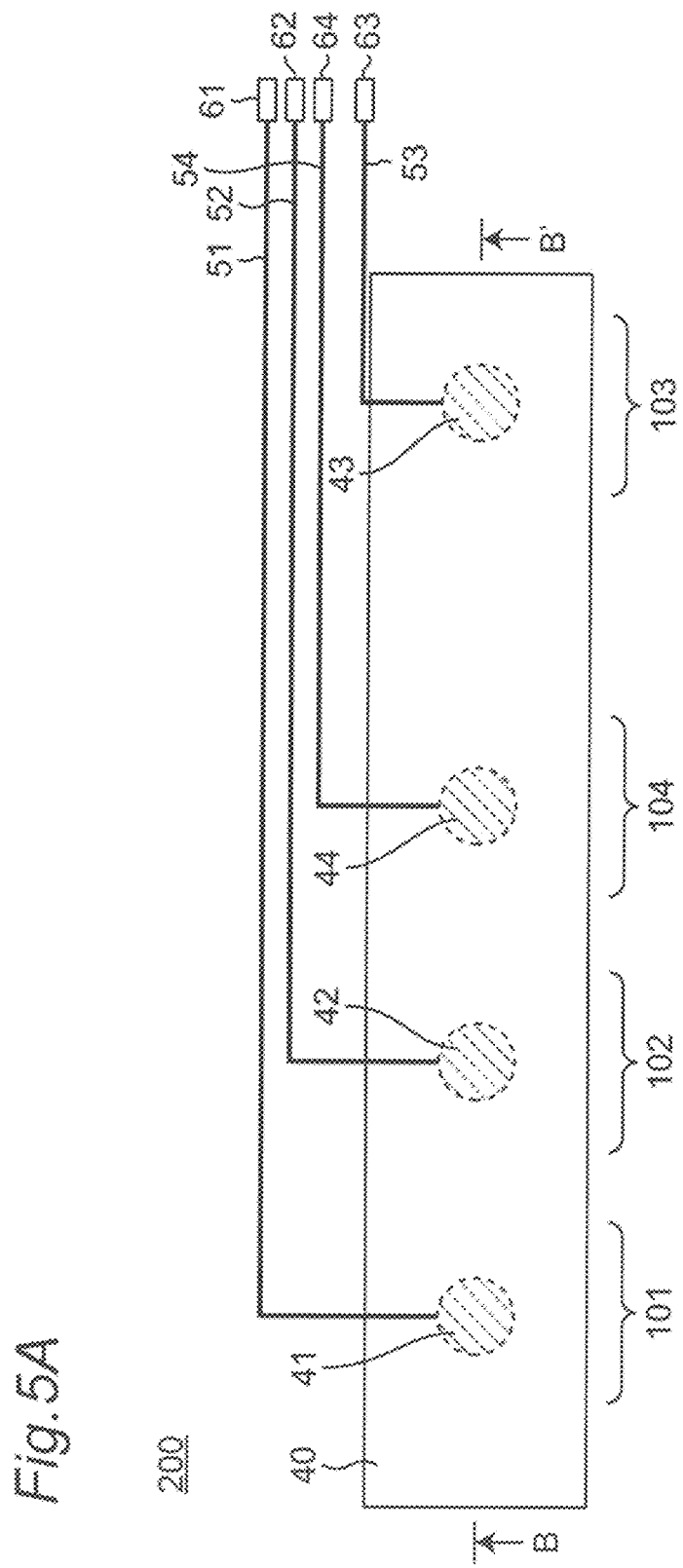

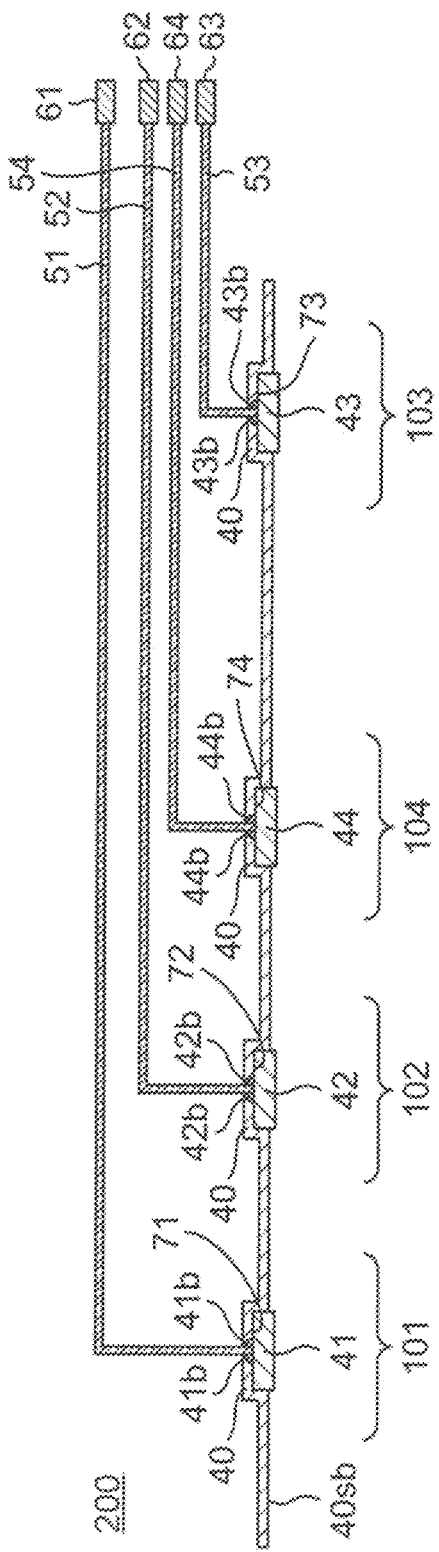

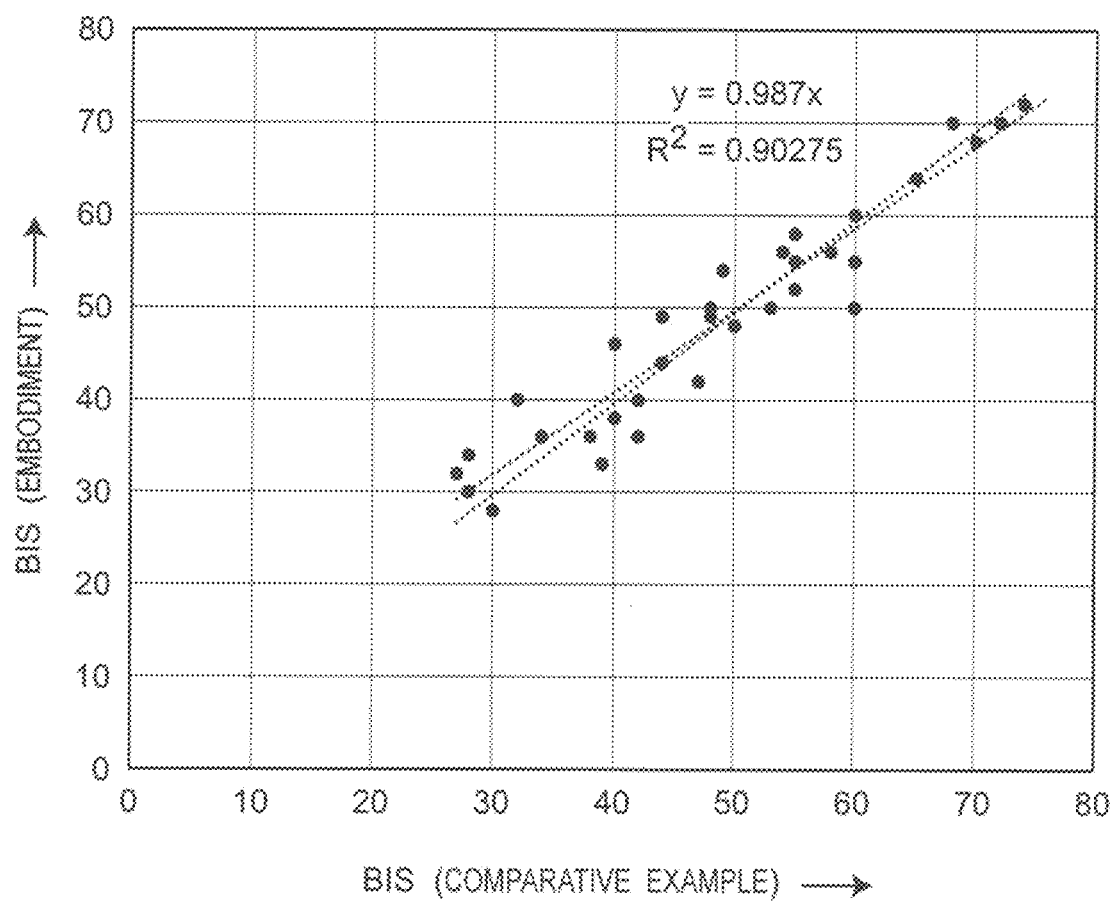

SENSOR CONNECTOR APPARATUS FOR USE IN ELECTROENCEPHALOGRAPHIC SPECTRUM ANALYZER, PROVIDED WITH CONDUCTIVE CONNECTION ELECTRODES CONNECTED TO SENSOR ELECTRODES

TECHNICAL FIELD

The present invention relates to a sensor connector apparatus for use in an electroencephalographic spectrum analyzer, such as a bispectral index monitoring apparatus ("bispectral index" is referred to as BIS, hereinafter) or a BIS processor, and a connection method using the sensor connector apparatus.

BACKGROUND ART

In order to prevent intraoperative awareness and maintain an adequate level of anesthetic depth, an anesthesia depth monitoring method using an electroencephalographic spectrum analyzer (for example, BIS-VISTA system or Entropy monitor) has been widely used in clinical anesthetics (See, for example, Non-patent Document 1, 2, and 3). In this case, an electroencephalographic spectrum analyzer, such as a BIS monitoring apparatus or a BIS processor, is disclosed, for example, in Patent Document 1 and Non-patent Documents 4 and 5. In addition, a "BIS Quatro sensor" used for an electroencephalographic spectrum analyzer is disclosed, for example, in Non-patent Document 6. Further, the applicant proposes an electroencephalographic sensor apparatus as disclosed in Patent Document 2.

FIG. 1 is a block diagram illustrating a configuration of an electroencephalographic monitoring system, including an electroencephalographic spectrum analyzer according to a prior art. In addition, FIG. 2 is a front view of a BIS Quatro sensor 100 of FIG. 1, illustrating an example configuration of the BIS Quatro sensor 100 and an example of mounting the BIS Quatro sensor 100.

Referring to FIG. 1, the BIS Quatro sensor 100 is attached to be mounted on a forehead 1 of a patient. The BIS Quatro sensor 100 includes a connector 15, The connector 15 is connected to a connector 2a of a patient interface cable 2, and then is connected through the patient interface cable 2 and a BIS processor 3 to reach a BIS monitor 4. In this case, the BIS Quatro sensor 100 also includes electroencephalographic sensor electrodes 11, 12, 13, and 14 (See FIG. 2), each of which detects an electroencephalographic signal. The BIS processor 3 amplifies, filters, and analyzes the electroencephalographic signal to output the analysis data result to display on the BIS monitor 4.

In this case, the BIS processor 3 calculates each indicator including a BIS based on the analysis of the electroencephalographic signal that is detected by the BIS Quatro sensor 100 from the forehead 1 of the patient. As commonly known, the HIS is calculated through a combination of four subparameters (BSR, QUAZI, Beta ratio, and SynchFastSlow) obtained by a time domain analysis, a frequency domain analysis, and a high order spectral analysis of the electroencephalographic signal.

FIG. 2 is the front view of the IS Quatro sensor 100 of FIG. 1, illustrating the example configuration of the BIS Quatro sensor 100 and the example of mounting the BIS Quatro sensor 100. Referring to FIG. 2, the BIS Quatro sensor 100 includes an adhesive pad sheet 10, a laminated, circuit board, and the connector 15. The laminate circuit board is formed on the adhesive pad sheet 10, and the connector 15 is connected to one end of the adhesive pad sheet 10. In this case, the adhesive pad sheet 10 has portions 10a, 10b, 10c, and 10d. The laminated circuit board includes the sensor electrodes 11 to 14, and connector wires 31, 32, 33 and 34 (See FIG. 4B). The sensor electrodes 11 to 14, each having a disc plate shape, are formed on the corresponding portions 10a to 10d, and are connected to the connector 15 via the corresponding connector wires 31 to 34. In FIG. 2, (1) the sensor electrode 11 is a first electrode,
(2) the sensor electrode 12 is a second electrode (ground electrode)
(3) the sensor electrode 13 is a third electrode, and
(4) the sensor electrode 14 is a fourth electrode.

In this case, the sensor electrodes 11 to 14 are arranged in an order of the sensor electrodes 11, 12, 14 and 13 from the connector 15.

PRIOR ART DOCUMENTS

Patent Documents

[Patent Document 1] Japanese Patent Laid-open Publication No. 2016-086972

[Patent Document 2] International Publication WO2012/017950A

Non-Patent Documents

[Non-patent Document 1] A. A. Dahaba et al., BIS-vista occipital montage in patients undergoing neurosurgical procedures during propofol-remifentanil anesthesia," Anesthesiology, Vol. 112. No. 3, March 2010, pp. 645-51.

[Non-patent Document 2] Shin Young Lee et al., "Comparison of bispectral index scores from the standard frontal sensor position with those from an alternative mandibular position," Korean Journal of Anesthesiology (Kja), Vol. 66, No. 4, April 2014, pp. 267-273.

[Non-patent Document 3] B. Brown et al., "Acceptability of auricular vs frontal bispectral index values,", British Journal of Anaesthesia (BJA), Volume 113, Issue 2, Aug. 1, 2004, pp. 296.

[Non-patent Document 4] Nihon Kohden Corporation, "BIS Processor QE-910P", Visceral Function Test Instrument, Controlled Medical Device, Controlled Medical Device Requiring Special Maintenance, and Electroencephalographic Spectrum Analyzer, Revised in April 2017 (Eighth Edition). (Searched on Sep. 29, 2017), Internet (URL=http://www.nihonkohden.co.jp/iryo/documents/pdf/H904285E.pdf)

[Non-patent Document 5] Nihon Kohden Corporation. "BIS Monitor Vista A-3000", Visceral Function Test Instrument, Controlled Medical Device, Controlled Medical Device Requiring Special Maintenance, and Electroencephalographic Spectrum Analyzer, Revised on 8 Nov. 2010 (Second Edition), [Searched on Sep. 29, 2017], Internet (URL=http://www.nihonkohden.co.jp/iryo/documcnta/pdf/HJ00114A.pdf)

[Non-patent Document 6] Covidien Japan Inc., "BIS Quatro Sensor", Visceral Function Test Instrument, Electroencephalographic Recording from Scalp Electrode, and General Medical Device, Revised on 2 Jul. 2012 (Sixth Edition), [Searched on Sep. 29, 2017], Internet (URL=http://www.covidien.co.jp/product_service/documents_pdf/RS-A5BISSN02(06).pdf)

SUMMARY OF THE INVENTION

Problems to be Solved by the Invention

In these circumstances, there is a case of performing a brain surgery or being unable to secure space suitable for attaching a cerebral oxygen saturation monitoring sensor and an electroencephalographic sensor, such as a BIS Quatro sensor, concurrently on the forehead 1 of the patient. In such a case, each sensor attachment area is crucial in terms of perioperative brain/neurological monitoring. However, no means of attaching to any other areas have been proved to be effective in obtaining an adequate waveform.

The present invention has been developed to solve such a problem. An object of the present invention is to provide a sensor connector apparatus for use in an electroencephalographic spectrum analyzer, and a connection method using the sensor connector apparatus, the sensor connector apparatus being simply attachable to, for example, a commercially available BIS Quatro sensor, capable of corresponding to a commercially available electroencephalographic spectrum analyzer, and further capable of favorably obtaining an electroencephalographic signal at accuracy higher than that of the prior art.

Solution to Problems

According to one aspect of the present invention, there is provided a sensor connector apparatus connected between an electroencephalographic spectrum analyzer and a sensor for use in the electroencephalographic spectrum analyzer, and the sensor connector apparatus includes a plurality of sensor connectors. Each of the sensor connectors includes a connector to be connected to the electroencephalographic spectrum analyzer; a connector lead, where the connector is connected to one end of the connector lead and a conductive connector electrode that is connected to another end of the connector lead, and is connected to, a sensor electrode of the sensor.

According to one aspect of the present invention, there is provided a connection method using a sensor connector apparatus connected between an electroencephalographic spectrum analyzer and a sensor for use in the electroencephalographic spectrum analyzer. The sensor connector apparatus includes a plurality of sensor connectors. Each of the sensor connectors includes: a connector to be connected to the electroencephalographic spectrum analyzer a connector lead, wherein the connector is connected to one end of the connector lead; a conductive connector electrode that is connected to the other end of the connector lead and is connected to a sensor electrode of the sensor; and a dielectric shoat that accommodates the plurality of conductive connector electrodes. Each of the conductive connector electrodes is provided directly beneath the dielectric sheet, and at a position to be connected to a corresponding one of the sensor electrodes of the sensor. The connection method includes a step of removably attaching the dielectric sheet on an adhesive surface of a pad sheet, the pad sheet having each of the sensor electrodes of the sensor thereon.

Effect of the Invention

Accordingly, the present invention provides a sensor connector apparatus for use in an electroencephalographic spectrum analyzer, and a connection method using the sensor connector apparatus. According to the present invention, the sensor connector apparatus is simply attachable to, for example, a commercially available BIS Quatro sensor, is capable of corresponding to a commercially available electroencephalographic spectrum analyzer, and further is capable of favorably obtaining an electroencephalographic signal at accuracy higher than that of the prior art.

BRIEF DESCRIPTION OF THE DRAWINGS

FIG. 4B is a longitudinal sectional view of the BIS Quatro sensor 100, taken along line A-A' of FIG. 4A.

FIG. 5A is a plan view illustrating an example schematic configuration of the sensor connector apparatus 200 of FIG. 3.

FIG. 5B is a longitudinal sectional view of the sensor connector apparatus 200, taken along line B-B' of FIG. 5A.

FIG. 78 is a photograph showing an appearance of a conductive connector electrode 41 and its vicinity in the sensor connector apparatus 200 of FIGS. 5A and 5B.

FIG. 9 is a graph showing experimental results of the BIS Quatro sensor 100 according to the prior art as a comparative example and the BIS sensor apparatus 300 according to the embodiment as an implementation example, the graph showing a correlation of a BIS obtained from the BIS Quatro sensor 100 according to the prior art and a BIS obtained from the BIS sensor apparatus 300 according to the embodiment.

MODE FOR CARRYING OUT THE INVENTION

Figure 1:
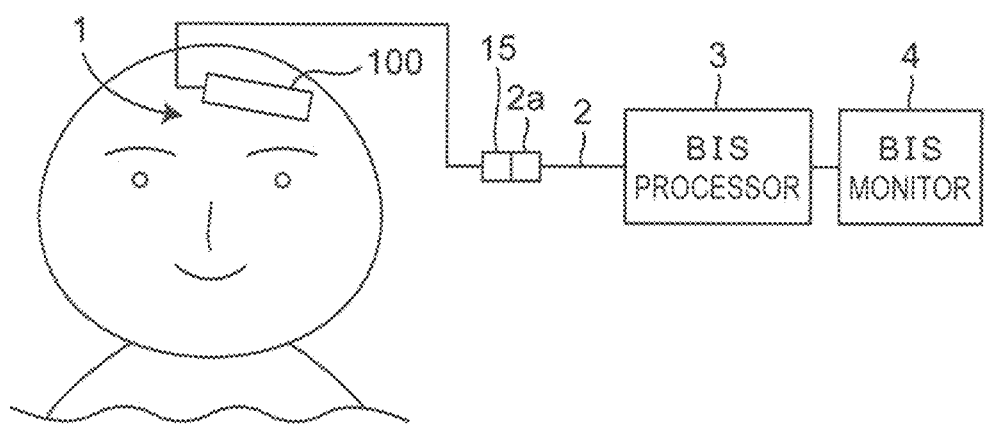
FIG. 1 is a block diagram illustrating a configuration of an electroencephalographic monitoring system, including an electroencephalographic spectrum analyzer, according to a prior art.

Hereinafter, an embodiment according to the present invention will be described with reference to the drawings. It should be noted that in the drawings, same reference characters represent identical constituent elements, and a detailed description thereof will be omitted.

An electroencephalographic spectrum analyzer such as a BIS monitoring system (See FIG. 1) is a clinical monitoring apparatus for measuring a BIS that is a numerical value showing a cerebral cortex activity related to level of consciousness based on a frequency, an amplitude, and an interference of a frontal lobe electroencephalographic signal. The BIS is mainly used for assessment of perioperative sedation level, and is applied to approximately 30% of all cases of general anesthesia in japan. BIS monitoring is presumed to optimize an amount of anesthetic so as to reduce a risk of postoperative complication caused by an overdose of anesthetic or a risk of intraoperative awareness caused by insufficient anesthesia.

When performing BIS monitoring, as illustrated in FIG. 1, a commercially available, standard adhesive electrode pad, such as a BIS Quatro sensor 100, is mounted on a forehead 1 of a patient. However, when the forehead 1 of the patient required to be an operative field or a clean field in brain surgery, or when an electroencephalographic spectrum analysis and cerebral oxygen saturation monitoring are concurrently performed, the forehead 1 of the patient is short of sensor attachment area, hindering the sensor from being mounted at an appropriate location. In this state, some reports said that the electrode pad was attached on the nose tip of the patient, the patient's lower jaw, back of the head of the patient, or the like. However, in these cases, BIS monitoring was not properly performed due to remote voltage potential inclusion or the like, causing degradation in validity of the waveform and value. By mounting sensor electrode on the forehead 1 of the patient in proximity to the frontal lobe, it is possible to perform BIS monitoring constantly. Even in the cases above, BIS monitoring is presumed to be reliably per so that safety in intraoperative treatment is increased.

Figure 3:
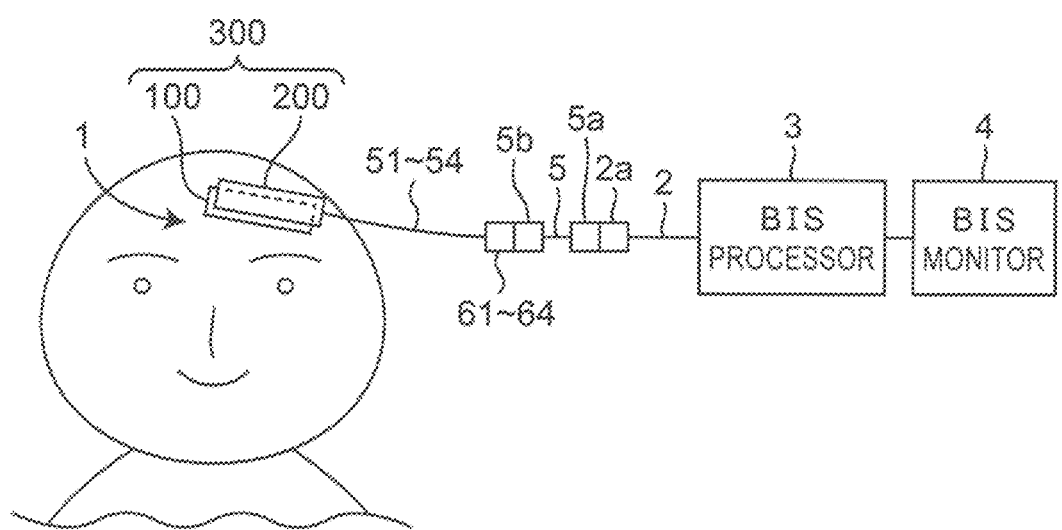
FIG. 3 is a block diagram illustrating an example configuration of an electroencephalographic monitoring system that includes a sensor connector apparatus 200 according to an embodiment of the present invention, while using the electroencephalographic spectrum analyzer.

FIG. 3 is a block diagram illustrating an example configuration of an electroencephalographic monitoring system that includes a sensor connector apparatus 200, while using a BIS processor 3 as an electroencephalographic spectrum analyzer. Referring to FIG. 3, the electroencephalographic monitoring system according to the embodiment includes the sensor connector apparatus 200 and a connector cable 5 between the BIS Quatro sensor 100 and the BIS processor 3, unlike the electroencephalographic monitoring system of FIG. 1.

Referring to FIG. 3, the sensor connector apparatus 200 is removably attached on an upper surface (adhesive surface) of the BIS Quatro sensor 100. The sensor connector apparatus 200 includes connector leads 51, 52, 53, and 54, and connectors 61, 52, 53, and 64. The connector leads 51 to 54 are connected to one end 5b of the connector cable 5 via the connectors 61 to 64. The connector cable 5 has the other end 5a that is connected to a patient interface cable 2 is a connector 2a and then connected to the BIS processor 3. The BIS Quatro sensor 100 includes electroencephalographic sensor electrodes 11, 12, 13, and 14 (See FIG. 2), each of which detects an electroencephalographic signal. The BIS processor 3 amplifies, filters, and analyzes the electroencephalographic signal to output the analysis data result to display on a BIS monitor 4. Referring to FIG. 3, the connector leads 51 to 54 are connected to the patient interface cable 2 via the connector cable 5, but it should be noted that the present invention is not limited to this configuration. Alternatively, the connector leads 51 to 54 may be directly connected to the patient interface cable 2.

Figure 2:
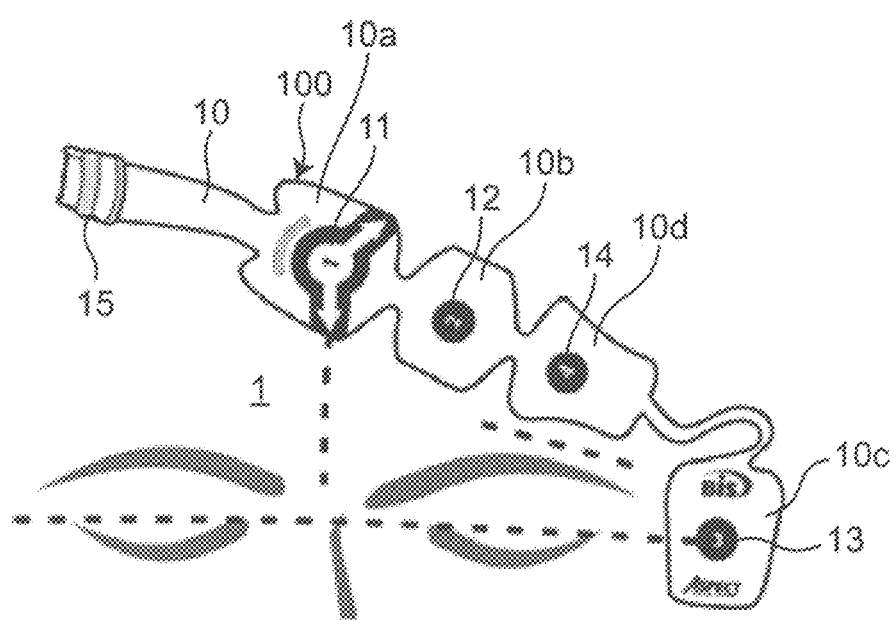
FIG. 2 is a front view of a BIS Quatro sensor 100 of FIG. 1, illustrating an example configuration of the BIS Quatro sensor 100 and an example of mounting the BIS Quatro sensor 100.
Figure 4A:
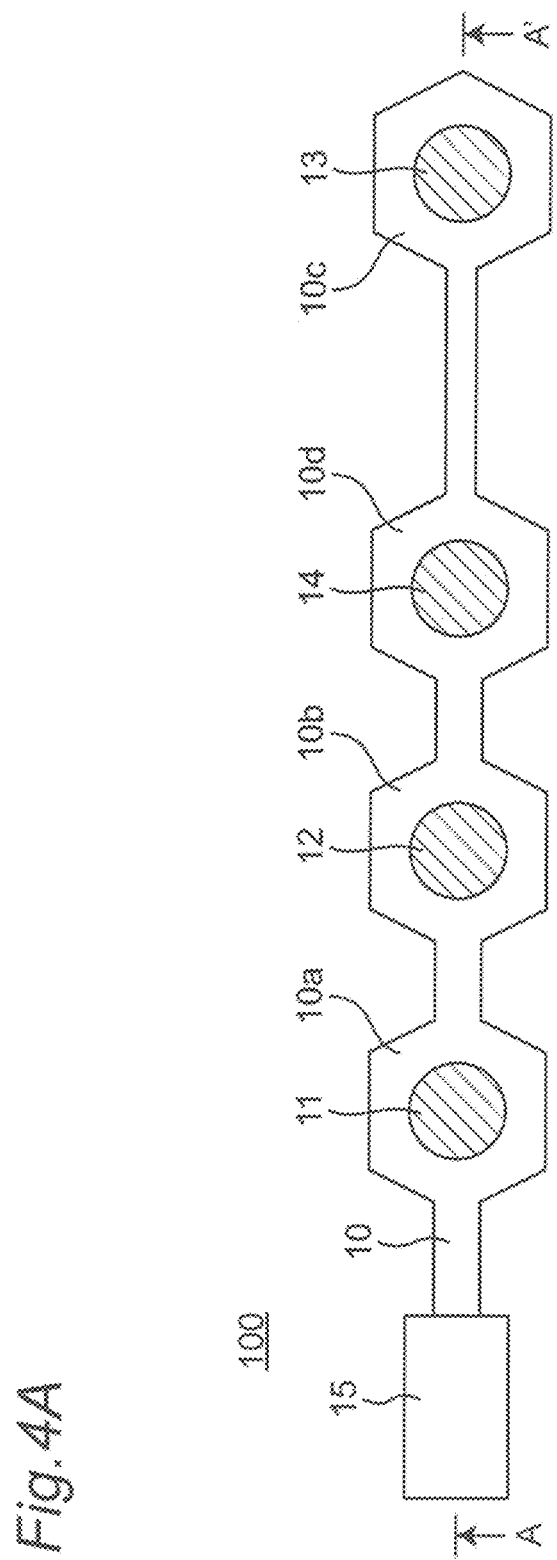
FIG. 4A is a plan view illustrating an example schematic configuration of the BIS Quatro sensor 100 of FIG. 2.

FIG. 4A is a plan view illustrating an example schematic configuration of the BIS Quatro sensor 100 of FIG. 2. FIG. 4B is a longitudinal sectional view of the BIS Quatro sensor 100, taken along line A-A' of FIG. 4A. Referring to FIGS. 4A and 4B, the BIS Quatro sensor 100 includes an adhesive pad sheet 10, the four sensor electrodes 11 to 14, and the connector 15. The adhesive pad sheet 10 is formed, for example, of an inducible pressure-sensitive adhesive material such as karaya gum, a silicone resin material, or a polyurethane material. The sensor electrodes 11 to 14, each having, for example, a circular flat-plate shape (disc plate shape), are formed on the adhesive pad sheet 10. The connector 15 is connected to one end of the adhesive pad sheet 10. The adhesive pad sheet 10 is constituted of an upper surface 10st as the adhesive surface, a bottom surface 10sb, four portions 10a, 10b, 10c, and 10d. Each of the four portions 10a to 10d has, for example, a regular hexagonal shape to increase an area for attachment so that the adhesiveness is increased. These portions 10a to 10d are connected adjoining each other linearly. Current collector substrates 21, 22, 23, and 24 are formed on the corresponding portions 10a to 10d, and the sensor electrodes 10a to 10d are formed on the corresponding current collector substrates 21 to 24. The sensor electrodes 11 to 14 are formed of a flexible material having a spongiform structure. Note that, the sensor electrodes 11 to 14 are electrically connected to the connector 15 via the corresponding current collector substrates 21 to 24.

FIG. 5A is a plan view illustrating an example schematic configuration of the sensor connector apparatus 200 of FIG. 3. FIG. 5B is a longitudinal sectional view of the sensor connector apparatus 200, taken along line B-B' of FIG. 5A. Referring to FIGS. 5A and 5B, the sensor connector apparatus 200 according to this embodiment is provided to connect the BIS Quatro sensor 100 with the BIS processor 3. The sensor connector apparatus 200 includes a flexible dielectric sheet 40 that is formed of a flexible dielectric material, such as a silicone resin material or a polyurethane material. The flexible dielectric sheet 40 includes a plurality (for example, four) of sensor connectors 101, 102, 103 and 104. In this case, each of the sensor connectors 101 to 104 includes:

(1) a corresponding one of the connectors 61 to 64 to connect the BIS Quatro sensor 100 with the BIS processor 3;

(2) a corresponding rime of the connector leads 51 to 54, to one end of which the corresponding one of the connectors 61 to 64 is connected;

(3) a corresponding one of conductive connector electrodes 41, 42, 43, and 44 that is connected to the other end of the corresponding one of the connector leads 51 to 54. The conductive connector electrodes 41, 42, 43 and 44 are also electrically surface-connected to the corresponding sensor electrodes 11 to 14 of the BIS Quatro sensor 100.

In this case, the conductive connector electrodes 41 to 44 are preferably formed of a highly conductive material (for example, silver, gold, or copper) or conductive aluminum, and formed in, for example, a circular flat-plate shape (disc plate shape). Each of the connector leads 51 to 54 is electrically connected at its tip to a corresponding one of the conductive connector electrodes 41 to 44 by corresponding one of, for example, bonding members 41b, 42b, 43b, and 44b or an adhesive. Each of the conductive connector electrodes 41 to 44 is accommodated in a corresponding one of a plurality (for example, four) of electrode mounting sections 71, 72, 73, and 74. The electrode mounting sections 71 to 74 are provided on a bottom surface side of the flexible dielectric sheet 40 and are each formed in a recess corresponding to the shape of the corresponding conductive connector electrodes 41 to 44.

Figure 6A:
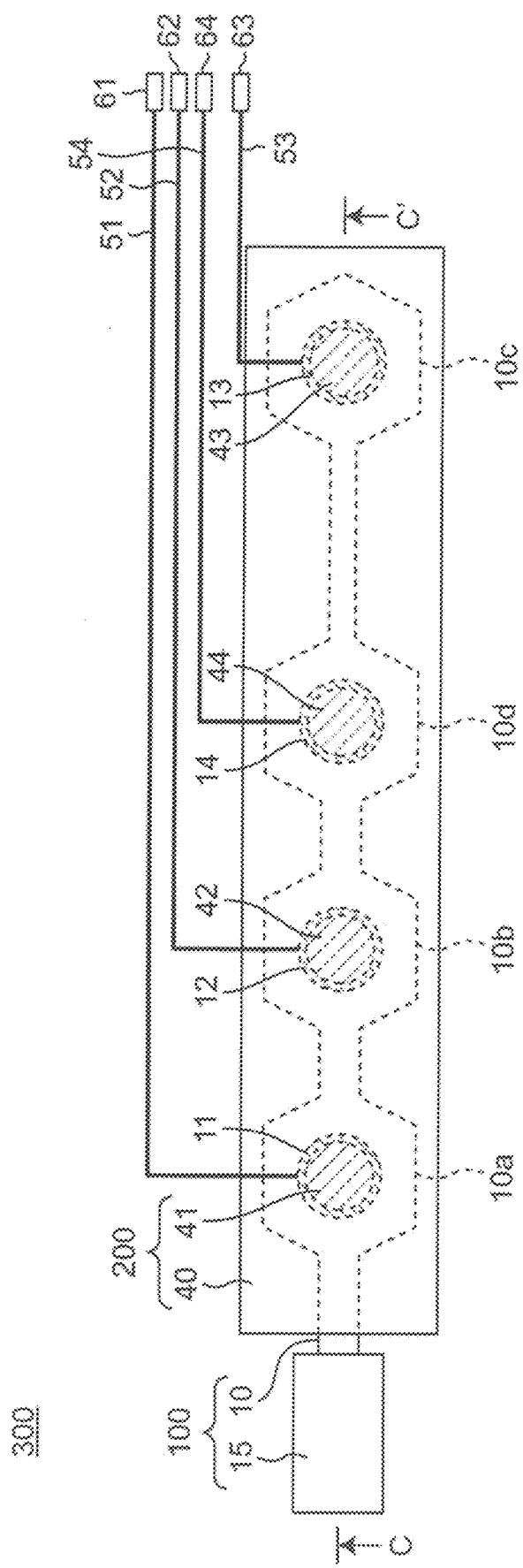
FIG. 6A is a pan view illustrating an example schematic configuration of a BIS sensor apparatus 300, in which the sensor connector apparatus 200 of FIGS. 5A and 5B is mounted on the BIS Quatro sensor 100 of FIGS. 4A and 4B.
Figure 6B:
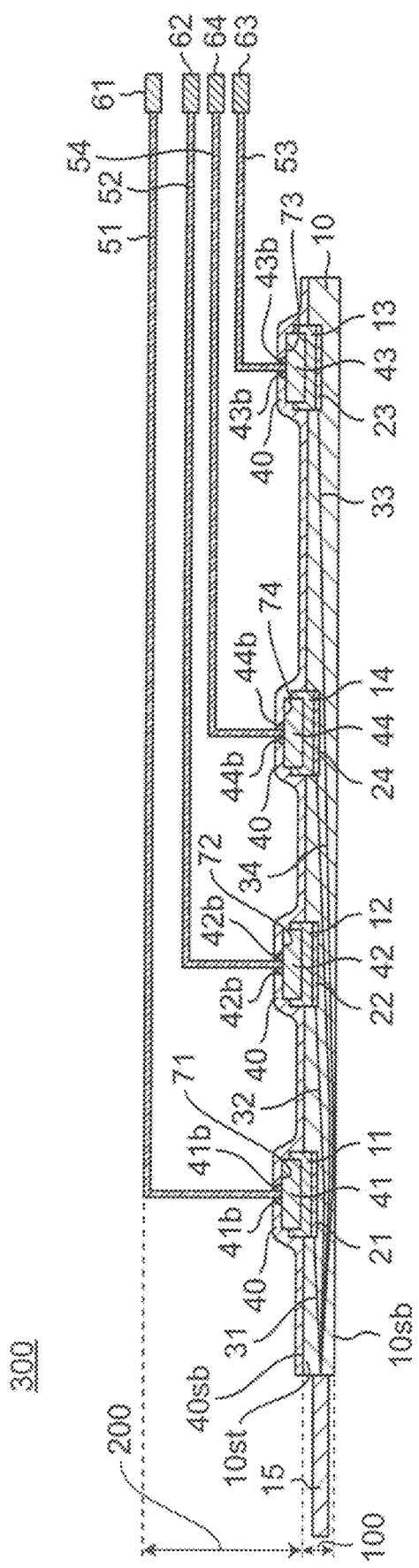
FIG. 6B is a longitudinal sectional view of the BIS sensor apparatus 300, taken along line C-C' of FIG. 6A.

FIG. 6A is a plan view illustrating an example schematic configuration of a BIS sensor apparatus 300, in which the sensor connector apparatus 200 of FIGS. 5A and 5B is mounted on the BIS Quatro sensor 100 of FIGS. 4A and 4B. In addition, FIG. 6B is a longitudinal sectional view of the BIS sensor apparatus 300, taken along line C-C' of FIG. 6A. Referring to FIGS. 6A and 6B, the flexible dielectric sheet 40 of the sensor connector apparatus 200 has a bottom surface 40sb that is disposed opposite the upper surface 10st (adhesive surface) of the BIS Quatro sensor 100, and the conductive connector electrodes 41 to 44 correspond to the sensor electrodes 11 to 14 so as to be electrically connected to the sensor electrodes 11 to 14. In this configuration, the sensor connector apparatus 200 is attached to the BIS Quatro sensor 100 to provide the combined BIS sensor apparatus 300.

Figure 7A:
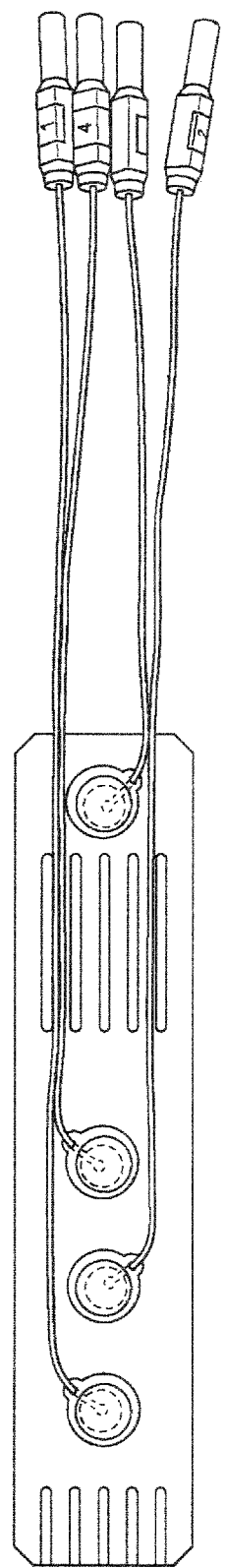
FIG. 7A is a photograph showing an appearance of the BIS sensor apparatus 300 of FIGS. 6A and 6B.

FIG. 7A is a photograph allowing an appearance of the BIS sensor apparatus 300 of FIGS. 6A and 6B.

Figure 7B:
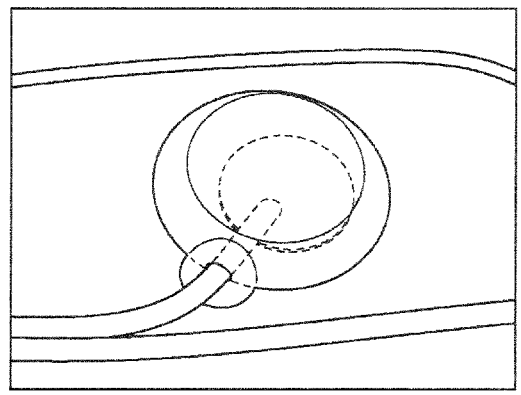
FIG. 7C is a photographic image taken from beneath the conductive connector electrode 41 of FIG. 7B.
Figure 7C:
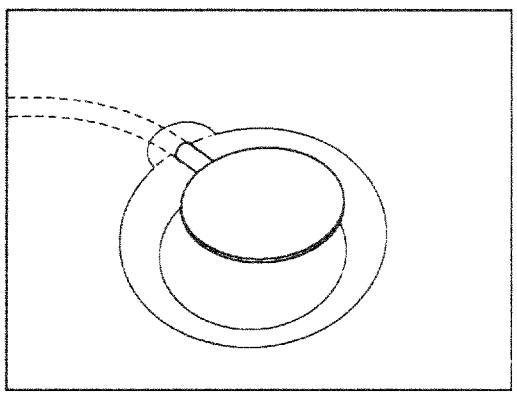

In addition, FIG. 7B is a photograph showing an appearance of the conductive connector electrode 41 and its vicinity in the sensor connector apparatus 200 of FIGS. 5A and 5B. FIG. 7C is a photographic, image taken from beneath the conductive connector electrode 41 of FIG. 7B. FIG. 7B shows an external view of the conductive connector electrode 41 as seen from above. FIG. 7C shows an external view of the conductive connector electrode 41 as seen from below.

Figure 8:
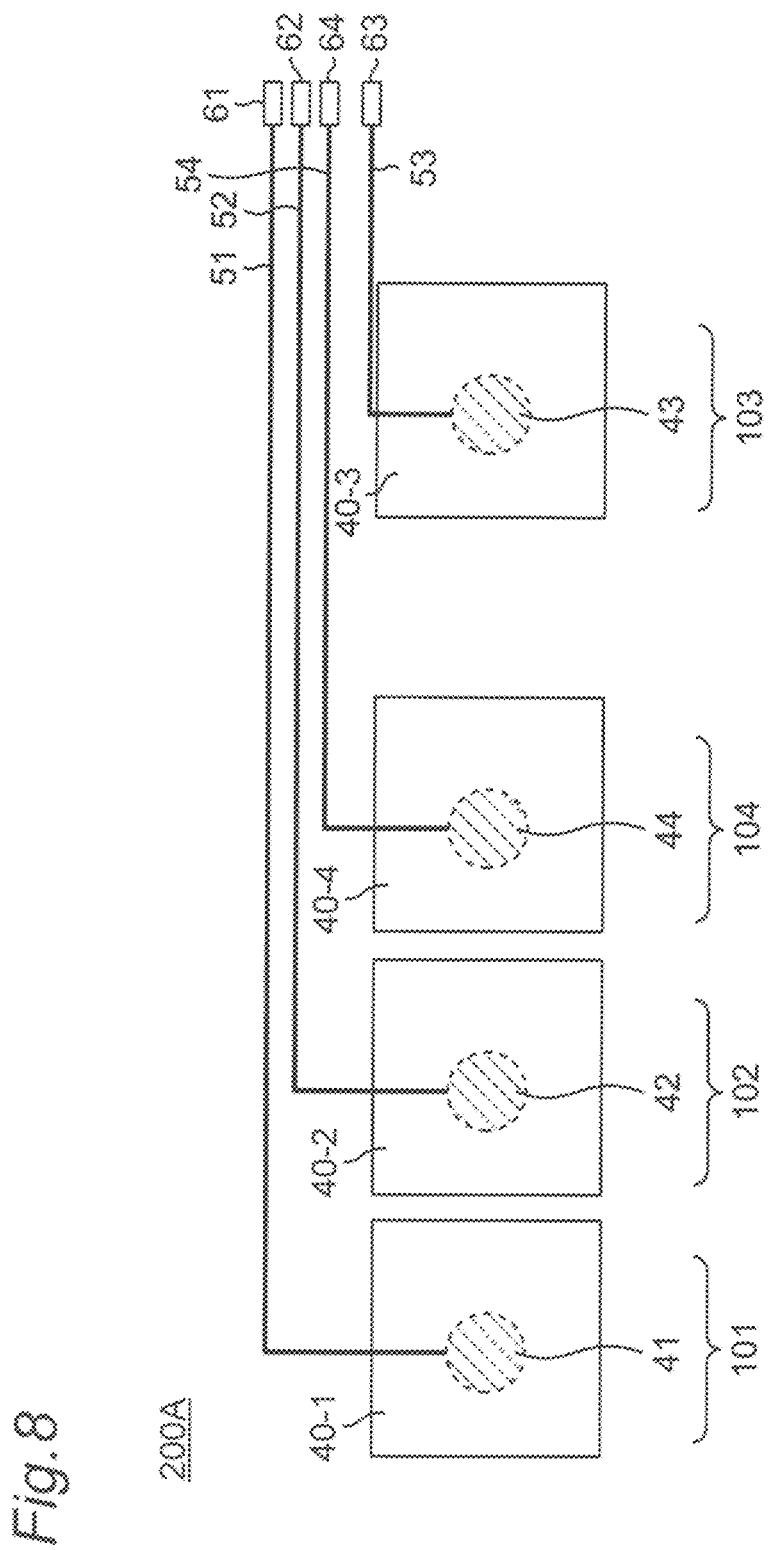
FIG. 8 is a plan view illustrating an example schematic configuration of a sensor connector apparatus 200A according to a modified embodiment.

FIG. 8 is a plan view illustrating an example schematic configuration of a sensor connector apparatus 200A according to a modified embodiment. With the sensor connector apparatus 200 of FIG. 5A, the four conductive connector electrodes 41 to 44 are accommodated in the flexible dielectric sheet 40 as a single dielectric sheet, but the present disclosure is not limited to this configuration. Alternatively, as illustrated in FIG. 8, the flexible dielectric sheet 40 may be divided into four dielectric sheets, 40-1, 40-2, 40-3, and 40-4. Then, the four dielectric sheets 40-1 to 40-4 may include, the corresponding sensor connectors 101 to 104, in which the corresponding conductive connector electrodes 41 to 44 may be accommodated.

In the foregoing embodiment, each of the sensor electrodes 11 to 14 has a disc plate shape, but the present invention is not limited to this configuration. Alternatively, the sensor electrodes 11 to 14 may be needle-shaped.

As described above, each of the sensor connector apparatus 200 according to this embodiment and the sensor connector apparatus 200A according to the modified embodiment, or the BIS sensor apparatus 300 as a combined form of the sensor connector apparatus 200 (or 200A) and the BIS Quatro sensor 100, provides advantageous functions and effects as follows:

(1) with the BIS sensor apparatus 300, the combined form of the sensor connector apparatus 200 (or 200A) and the BIS Quatro sensor 100, it is possible to measure an electroencephalographic signal from the forehead 1 of the patient, which is highly recommended;

(2) the apparatus is simply attachable to a commercially available sensor, such as the BIS Quatro sensor 100;

(3) the apparatus is capable of corresponding to each of a disc electrode and a needle electrode of a commercially available sensor such as the BIS Quatro sensor 100;

(4) the apparatus is capable of corresponding to any one of commercially available electroencephalographic spectrum analyzers such as the BIS processor 3; and (5) each of the sensor connector apparatus 200 and 200A is easily provided at reasonable cost and high versatility.

IMPLEMENTATION EXAMPLE

1. Object of Implementation Example

The present inventor prepared a sensor connector apparatus 200 (See FIGS. 4A and 4B) as a novel technique, namely, "a disc (or needle) electrode conversion device connectable to an electroencephalographic spectrum analyzer (for example, BIS-VISTA system or Entropy monitor)" so as to verify the clinical effectiveness.

2. Preparation of the Apparatus

In clinical use, a BIS Quatro sensor 100 was attached on a forehead 1 of a patient for impedance check. In this state, BIS monitoring did not start without having sufficient electrical conductivity. In a case of the sensor connector apparatus 200 according to this embodiment, an impedance problem was identified in two areas as follows:

(A) an contact area A between sensor electrodes 11 to 14 and conductive connector electrodes 41 to 44, and (B) a contact area B between the sensor electrodes 11 to 14 and skin of the patient.

In this case, the contact area B was already clinically applicable, but electrical conductivity of the contact area A was still a concern. In the measurement to check on electrical conductivity of the commercially available sensor, each value of electrode resistance required by a BIS processor 3 was as follows. Here, "pass" indicates a condition where a set of predetermined criteria was fulfilled. In this case, an impedance measurement for each single electrode was performed between a tip of the corresponding connector lead and the electrode. The impedance measurement between each pair of the electrodes was performed between the corresponding connector leads connected to the electrodes.

(1) Each of the conductive connector electrodes 41 to 44 showed an impedance value less than 7.5 kΩ, and the electrical conductivity was "pass".

(2) The conductive connector electrode 42 as a ground electrode showed an impedance value less than 30 kΩ, and the electrical conductivity was "pass".

(3) When each of an impedance between the conductive connector electrodes 41 and 43 and an impedance between the conductive connector electrodes 41 and 44 showed a value of 15 kΩ or less, and when the conductive connector electrode 42 showed the impedance value less than 30 kΩ, the electrical conductivity was judged "pass".

In this case, the impedance check condition was set at a frequency of 128 Hz and a current of approximately 1 nA (0.001 μA). By following these conditions and taking electrical conductivity, cost-effectiveness, and simplicity of the preparation into account, a prototype sensor connector apparatus 200 below was prepared.

First Implementation Example

Prototype 1: Stainless Steel Electrode

First, stainless steel, being available at lowest cost, was applied to the conductive connector electrodes 41 to 44 upon preparing a sensor connector apparatus 200. The BIS Quatro sensor 100, a commercially available sensor including electroencephalographic electrodes, was used. The sensor connector apparatus 200 was attached on the BIS Quatro sensor 100 to constitute a BIS sensor apparatus 300. Next, the BIS sensor apparatus 300 was immersed in saline solution and subjected to impedance check. However, in this implementation example, "Noise" was displayed on a BIS monitor 4, and thus the apparatus did not "pass".

As a disposable bioelectrode, a silver/silver chloride printed sensor electrode is typically employed. The sensor connector apparatus 200 was attached to the disposable bioelectrode (via gel) to constitute a BIS sensor apparatus, and the conductivity was tested. Presumably, in this state, due to a combination of the different metals, a voltage potential difference (of several tens to 100 mV) arose. As a result, each of the voltage potential difference and a fluctuation in the voltage potential difference was included in a signal from the needle electrode, causing the not "pass" result.

Second Implementation Example

Prototype 2: Silver/Silver Chloride Electrode

Most preferably, the metals were placed directly (not via gel) in contact with each other, but pharmaceutically, a commercially available sensor is not permitted to be modified. Instead of a stainless steel plate, a silver/silver chloride plate, being presumed to be identical to the electrodes of the BIS Quatro sensor 100, was used. In this case, a silver/silver chloride plate was used as each of the conductive connector electrodes 41 to 44 upon preparing a sensor connector apparatus 200. The BIS Quatro sensor 100, commercially available sensor including the electroencephalographic electrodes, was used. The sensor connector apparatus 200 was attached on the BIS Quatro sensor 100 to constitute a BIS sensor apparatus 300.

In the BIS sensor apparatus 300, a combined form of the BIS Quatro sensor 100 and the sensor connector apparatus 200 including the conductive connector electrodes 41 to 44 (to which silver/silver chloride was applied), the measurement by use of an impedance meter resulted as follows. An impedance between each pair of the corresponding electrodes (namely, between 11 and 41, between 12 and 42, between 13 and 43, and between 14 and 44) showed a value of approximately 100Ω, and was thus considered to be satisfactory to "pass". However, the impedance check resulted in a value of 1000Ω. This implementation example showed a certain degree of improvement compared with the stainless steel electrode that ended as unmeasurable. Still, the BIS monitor 4 displayed high impedance with large noise and thus, the silver/silver chloride electrode was not satisfactory to "pass".

In this case, each of the sensor electrodes 11 to 14 of the BIS Quatro sensor 100, having an identical silver color to the connector wires 31 to 34, may be formed of silver instead of salver/silver chloride. In case that the sensor electrodes 11 to 14 are formed of silver, the voltage potential difference of several tens of mV between the silver and the silver/silver chloride may be generated.

Third Implementation Example

Prototype 3: Silver Electrode

Upon preparing this prototype sensor connector apparatus 200, a silver plate was used as each of the conductive connector electrodes 41 to 44. Then, the BIS Quatro sensor 100 and the sensor connector apparatus 200 including the conductive connector electrodes 41 to 44 (to which silver was applied) were combined to constitute a BIS sensor apparatus 300. The BIS sensor apparatus 300 was subjected to impedance check in a manner similar to that of the first implementation example and the second implementation example. Here, even the measurement result displayed on the BIS monitor 4 showed a resistance value of 10Ω or less, so that the BIS sensor apparatus 300 was proved to be applicable for monitoring.

Each of connector leads 51 to 54 serving as a relay cis well as each of the conductive connector electrodes 41 to 44 as a silver plate electrode are basically available for long-term use, as long as none of these is disconnected. After being used in connecting each of the connector leads 51 to 54 serving as the relay with an input electrode for the BIS processor 3, each of the conductive connector electrodes 41 to 44 as the silver plate is preferably cleaned with cotton with alcohol, flowing water, or the like so that jelly-like electrode paste or the like is washed off the surface. Then, the conductive connector electrodes 41 to 44 are left to dry to be ready for next use so as to be available for use at frequent times.

Preparation of a simple device for impedance check;

When each prototype BIS sensor apparatus 300 (including the conductive connector electrodes 41 to 44 and the connector leads 51 to 54) was wholly subjected to impedance check, each of the conductive connector electrodes 41 to 44 as a disc electrode (or needle electrode) was immersed in saline solution. As previously described, the impedance problem was identified in the contact area between each of the sensor electrodes 11 to 14 and a corresponding one of the conductive connector electrodes 41 to 44. By taking into account that reuse of the device may cause a change in the resistance in the contact area, the prototype BIS sensor apparatus 300 was connected to the input electrode for the BIS processor 3 via each of the connector leads 51 to 54. Then, a short circuit was created on input cords (including four DIN connectors) from the connector leads 51 to 54 serving as the relay, and another circuit was created to perform a simple "pass" confirmation (including confirmation of the connector leads 51 to 54 as the relay) on the BIS monitor 4 and the BIS processor 3.

Results of Clinical Measurement

The BIS sensor apparatus 300 according to dais embodiment (the combined form of the BIS Quatro sensor 100 and the sensor connector apparatus 200) was subjected to the clinical measurement so as to verify the clinical effectiveness.

FIG. 9 is a graph showing experimental results of the BIS Quatro sensor 100 according to the prior art as a comparative example and the BIS sensor apparatus 300 according to the embodiment as an implementation example. FIG. 9 shows a correlation of a BIS obtained front the BIS Quatro sensor 100 according to the prior art and a BIS obtained from the BIS sensor apparatus 300 according to the embodiment.

The BIS obtained from the BIS sensor apparatus 300 including the sensor connector apparatus 200 according to this embodiment was compared with the BIS obtained from the BIS Quatro sensor 100 according to the prior art as a commercially available sensor. As a result, as seen from FIG. 9, an excellent positive correlation was obtained between these BISs (with a regression line of y=0.987x, and a correlation coefficient of $R^2$=0.90275).

Modified Embodiments

In the foregoing embodiment, the BIS processor 3 is provided, but the present invention is not limited to this configuration. Alternatively, any other types of electroencephalographic spectrum analyzers may be provided.

In the foregoing embodiment, the BIS Quatro sensor 100 is provided, but the present invention is not limited to this configuration. Alternatively, any other types of electroencephalographic sensors may be provided.

INDUSTRIAL APPLICABILITY

As mentioned above in detail, the present invention provides a sensor connector apparatus for use in an electroencephalographic spectrum analyzer, and a connection method using the sensor connector apparatus. According to the present invention, the sensor connector apparatus is simply attachable to, for example, a commercially available BIS Quatro sensor, is capable of corresponding to a commercially available electroencephalographic spectrum analyzer, and further Is capable of favorably obtaining an electroencephalographic signal at accuracy higher than that of the prior art.

The invention claimed is:

1. A sensor connector apparatus to be connected between an electroencephalographic spectrum analyzer and a sensor for use in the electroencephalographic spectrum analyzer, the sensor connector apparatus comprising a plurality of sensor connectors,
wherein each of the sensor connectors comprises:
a connector to be connected to the electroencephalographic spectrum analyzer;
a connector lead, wherein the connector is connected to one end of the connector lead; and
a conductive connector electrode that is connected to another end of the connector lead, and is to be connected to a sensor electrode of the sensor,
wherein the sensor connector apparatus further comprises a dielectric sheet that accommodates the plurality of conductive connector electrodes to cover the plurality of conductive connector electrodes,
wherein each of the conductive connector electrodes is provided directly beneath the dielectric sheet and at a position to be directly connected to a corresponding one of the sensor electrodes of the sensor, and
wherein the dielectric sheet is to be removably attached on an adhesive surface of a pad sheet of the sensor, the pad sheet having each of the sensor electrodes of the sensor thereon.

2. The sensor connector apparatus as claimed in claim 1, wherein the electroencephalographic spectrum analyzer is a bispectral index (BIS) processor,
wherein the sensor is an electroencephalographic sensor to be connected to the BIS processor, and
wherein the connector is connected to a sensor electrode of the electroencephalographic sensor.

3. The sensor connector apparatus as claimed in claim 1, wherein the dielectric sheet comprises a plurality of electrode mounting sections, each of the electrode mounting sections being formed in a recess shape corresponding to a shape of a corresponding one of the conductive connector electrodes so that the conductive connector electrodes are mounted.

4. A connection method using a sensor connector apparatus connected between an electroencephalographic spectrum analyzer and a sensor for use in the electroencephalographic spectrum analyzer,
wherein the sensor connector apparatus comprises a plurality of sensor connectors,
wherein each of the sensor connectors comprises:
a connector to be connected to the electroencephalographic spectrum analyzer;
a connector lead, wherein the connector is connected to one end of the connector lead;
a conductive connector electrode that is connected to the other end of the connector lead and is connected to a sensor electrode of the sensor; and
a dielectric sheet that accommodates the plurality of conductive connector electrodes to cover the plurality of conductive connector electrodes,
wherein each of the conductive connector electrodes is provided directly beneath the dielectric sheet, and at a position to be directly connected to a corresponding one of the sensor electrodes of the sensor, and
wherein the connection method comprising the step of removably attaching the dielectric sheet on an adhesive surface of a pad sheet, the pad sheet having each of the sensor electrodes of the sensor thereon.

5. The connection method using the sensor connector apparatus as claimed in claim 4,
wherein the dielectric sheet comprises a plurality of electrode mounting sections, each of the electrode mounting sections being formed in a recess shape corresponding to a shape of one of the conductive connector electrodes, and
wherein the step of attaching comprises attaching the dielectric sheet on the adhesive surface of the pad sheet so that each of the conductive connector electrodes corresponds to a corresponding one of the sensor electrodes so as to be electrically connected to the corresponding one of the sensor electrodes.

* * * * *